United States Patent
Kron et al.

(10) Patent No.: US 8,123,802 B2
(45) Date of Patent: Feb. 28, 2012

(54) SADDLE-SHAPED MITRAL VALVE ANNULOPLASTY PROSTHESES WITH ASYMMETRY, AND RELATED METHODS

(75) Inventors: Irving L. Kron, Charlottesville, VA (US); Melinda Kaye Kovach, Plymouth, MN (US); Timothy John McGill, Minneapolis, MN (US); Nathaniel Zacharias Zenz-Olson, Blaine, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 12/870,252

(22) Filed: Aug. 27, 2010

(65) Prior Publication Data

US 2010/0324670 A1 Dec. 23, 2010

Related U.S. Application Data

(62) Division of application No. 11/585,483, filed on Oct. 24, 2006, now abandoned.

(60) Provisional application No. 60/730,297, filed on Oct. 26, 2005.

(51) Int. Cl.
*A61F 2/24* (2006.01)

(52) U.S. Cl. ...................... 623/2.36; 623/2.37

(58) Field of Classification Search .................. 623/2.36, 623/2.37; A61F 2/24
See application file for complete search history.

(56) References Cited

U.S. PATENT DOCUMENTS

| | | | |
|---|---|---|---|
| 6,726,717 B2 | 4/2004 | Alfieri et al. | |
| 6,797,002 B2 | 9/2004 | Spence et al. | |
| 6,805,710 B2 | 10/2004 | Bolling et al. | |
| 6,858,039 B2 | 2/2005 | McCarthy | |
| 2001/0021874 A1 | 9/2001 | Carpentier et al. | |
| 2003/0083742 A1 | 5/2003 | Spence et al. | |
| 2003/0208264 A1 | 11/2003 | McCarthy et al. | |
| 2004/0006384 A1 | 1/2004 | McCarthy | |
| 2005/0131533 A1 | 6/2005 | Alfieri et al. | |
| 2005/0256567 A1 | 11/2005 | Lim et al. | |
| 2005/0256568 A1 | 11/2005 | Lim et al. | |
| 2005/0256569 A1 | 11/2005 | Lim et al. | |
| 2005/0267572 A1 | 12/2005 | Schoon et al. | |
| 2005/0278022 A1 | 12/2005 | Lim | |
| 2006/0100697 A1 | 5/2006 | Casanova | |

FOREIGN PATENT DOCUMENTS

| | | |
|---|---|---|
| EP | 0595791 A2 | 5/1994 |
| EP | 0860151 A1 | 8/1998 |
| WO | 03/041617 A1 | 5/2003 |

*Primary Examiner* — Thomas J Sweet
*Assistant Examiner* — Jason-Dennis Stewart
(74) *Attorney, Agent, or Firm* — Lerner, David, Littenberg, Krumholz & Mentlik, LLP

(57) ABSTRACT

A mitral valve annuloplasty prosthesis (ring or C) has a generally saddle shape, i.e., portions of the prosthesis that are or will be adjacent the anterior and posterior commissures of the valve are relatively low as compared to at least some other portions of the prosthesis that are or will be between the commissures. However, the saddle shape is asymmetrical, in that the portion that is or will be adjacent the posterior commissure is lower than the portion that is or will be adjacent the anterior commissure.

5 Claims, 7 Drawing Sheets

SADDLE-SHAPED MITRAL VALVE ANNULOPLASTY PROSTHESES WITH ASYMMETRY, AND RELATED METHODS

CROSS-REFERENCE TO RELATED APPLICATIONS

The present application is a divisional of U.S. patent application Ser. No. 11/585,483, filed Oct. 24, 2006, which claims the benefit of U.S. provisional patent application No. 60/730,297, filed Oct. 26, 2005, the disclosures of which are hereby incorporated by reference herein in their entirety.

FIELD OF THE INVENTION

This invention relates generally to medical devices, and in particular, to annuloplasty rings and other similar prostheses for reshaping the mitral valve annulus of a patient's heart. The invention also relates to methods of using such prostheses.

BACKGROUND OF THE INVENTION

The mitral annulus represents the junction of the fibrous and muscular tissue that joins the left atrium and the left ventricle. The mitral valve is a bicuspid valve having a relatively large anterior leaflet that coapts or meets with a smaller posterior leaflet.

FIG. 1 illustrates a normal mitral heart valve 14 from the left atrium from a surgical view of the heart. The anterior portion A of the mitral annulus 15 forms a part of the "cardiac skeleton" and is bounded by anterior and posterior commissures 16, 17. The anterior commissure 16 and posterior commissure 17 are generally at the junction points of the anterior leaflet 18 and the posterior leaflet 19. The junction points are also known as the anterolateral commissure 16 and posteromedial commissure 17. The posterior portion P of the mitral annulus 15 consists mainly of muscular tissue of the outer wall of the heart.

Referring to FIGS. 1 and 2, posterior leaflet 19 is divided into three scallops indicated as P1, P2, and P3 in sequence from the anterior commissure 16 counterclockwise to the posterior commissure 17. Anterior leaflet 18 is also divided into three areas indicated as A1, A2, and A3 in sequence from the anterior commissure 16 clockwise to the posterior commissure 17.

Ischemic heart disease can cause a mitral valve to become incompetent. In patients who suffer from cardiomyopathy due to ischemia, regions of the left ventricle lose their contractility and dilate. As the disease progresses, the left ventricle enlarges and becomes more round in shape, going from a conical shape to more of a spherical shape. Referring to FIG. 2, papillary muscles 23, 25 are displaced down (inferiorly) and away from each other. The change in the location of the papillary muscles increases the distance between the papillary muscles and the mitral valve annulus. This creates tension on the chordae tendonae 21 that connect the posterior papillary muscle 23 to the mitral valve leaflets in the A2, A3, P2, and P3 regions of the annulus. Since the chordae tendonae 21 do not change their length significantly, the chordae 21 tend to pull or "tether" the mitral leaflets. In severe cases of left ventricle dilation, the tethering of the chordae prevents the leaflets from coming together or coapting correctly, resulting in mitral valve regurgitation. In addition to remodeling of the left ventricle, the mitral valve tends to flatten during ventricular systole instead of achieving its natural saddle shape. This also disrupts the natural coaptation of the mitral leaflets and the natural distribution of stresses over the leaflets and chordae tendonae.

In ischemic mitral regurgitation (IMR), the entire circumference of the mitral annulus may dilate. The posterior portion of the annulus may dilate more than the anterior portion because the anterior portion has more support from the heart's fibrous skeleton. In cases where IMR is caused by posteromedial myocardial infarction, there may be an asymmetric dilation of the posteromedial annulus, which is indicated at A2, A3, P2, and P3. In this case, the IMR may be caused by tethering of leaflet segments connected to the posteromedial papillary muscle. This is often in the A2, A3, P2, and P3 segments of the mitral valve.

Often, this type of mitral valve regurgitation is surgically repaired with an annuloplasty ring (which may be either a complete ring or a C-shaped "ring" with an opening along the anterior side). The repair restores proper leaflet coaptation by decreasing the diameter of the mitral valve annulus, thereby mitigating the effect of the tethering of the chordae and the effects of dilation of the annulus. One surgical correction for IMR is to tether the posteromedial annulus of the mitral valve to the posteromedial papillary muscle. This papillary muscle relocation procedure reduces the chordal tension and allows the leaflets to coapt more effectively.

SUMMARY OF THE INVENTION

In accordance with the present invention, patient conditions like those described above are treated by applying an annuloplasty prosthesis (ring or C) that is shaped to push down the mitral valve annulus in the vicinity of the posterior commissure relative to other portions of the annulus. The prosthesis also dips down adjacent the anterior commissure, but it pushes down the portion of the annulus that is adjacent the posterior commissure farther than it dips down adjacent the anterior commissure. The effect of the prosthesis on the two commissure regions of the annulus is therefore asymmetrical.

A mitral valve annuloplasty ring in accordance with the invention includes A1, A2, A3, P3, P2, and P1 segments connected to one another in a closed loop series in the order just mentioned. Each of these ring segments is configured for placement adjacent the portion of a mitral valve annulus that is adjacent the corresponding A1, A2, A3, P3, P2, or P1 segment of the mitral valve leaflets. The ring has an anterior-to-posterior ("AP") axis that extends across the ring from its anterior (A1/A2/A3) side to its posterior (P1/P2/P3) side. The AP axis is perpendicular to a line between two reference points that are spaced from one another along the anterior side of the ring. The AP axis also bisects this line. These two reference points are located along the anterior side of the ring so that the AP axis also bisects a greatest width dimension of the ring, which greatest width dimension is measured perpendicular to the AP axis. A third reference point is located along the posterior side of the ring to one side of the AP axis (e.g., the side that is toward or closer to the anterior commissure). Each of the above-mentioned three reference points is spaced from the AP axis by 0.5 mm. These three reference points lie in and thereby define a reference plane. A point on the ring between the A1 and P1 segments, and another point on the ring between the A3 and P3 segments are both displaced from the reference plane to the same side of that plane. The amount of displacement from the reference plane to the point between the A3 and P3 segments is greater than the amount of displacement from the reference plane to the point between the A1 and P1 segments.

Instead of being a complete ring as described above, an annuloplasty prosthesis in accordance with the invention may have a C shape. This C shape can be similar to a complete ring in accordance with the invention, but with a portion of the anterior side of the ring omitted. The gap in the C that results from this omission is generally located approximately centrally on the anterior side of the C structure. The anterior side of the C may be thought of as defining a trajectory that includes both the anterior structure (i.e., comparable to at least portions of the A1 and A3 segments of a comparable ring) and a smooth continuation, across the gap, of both of those anterior structural segments. This trajectory follows a path through the gap that would be occupied by material of the prosthesis if the C were instead a complete ring in accordance with the invention. The summary description provided above for the various reference points and the reference plane of a complete ring applies again to such a C, with the exception that the first and second reference points need to be described as being on the above-mentioned trajectory because they may lie either in anterior material of the prosthesis (if the gap is relatively small) or in the gap (if the gap is relatively large).

Further features of the invention, its nature and various advantages, will be more apparent from the accompanying drawings and the following detailed description.

BRIEF DESCRIPTION OF THE DRAWINGS

FIG. 3 shows the ring having the same orientation as FIG. 1 shows a mitral valve with which the ring may be used, but the scale of FIG. 3 is larger than the scale of FIG. 1.

DETAILED DESCRIPTION

Figure 1:
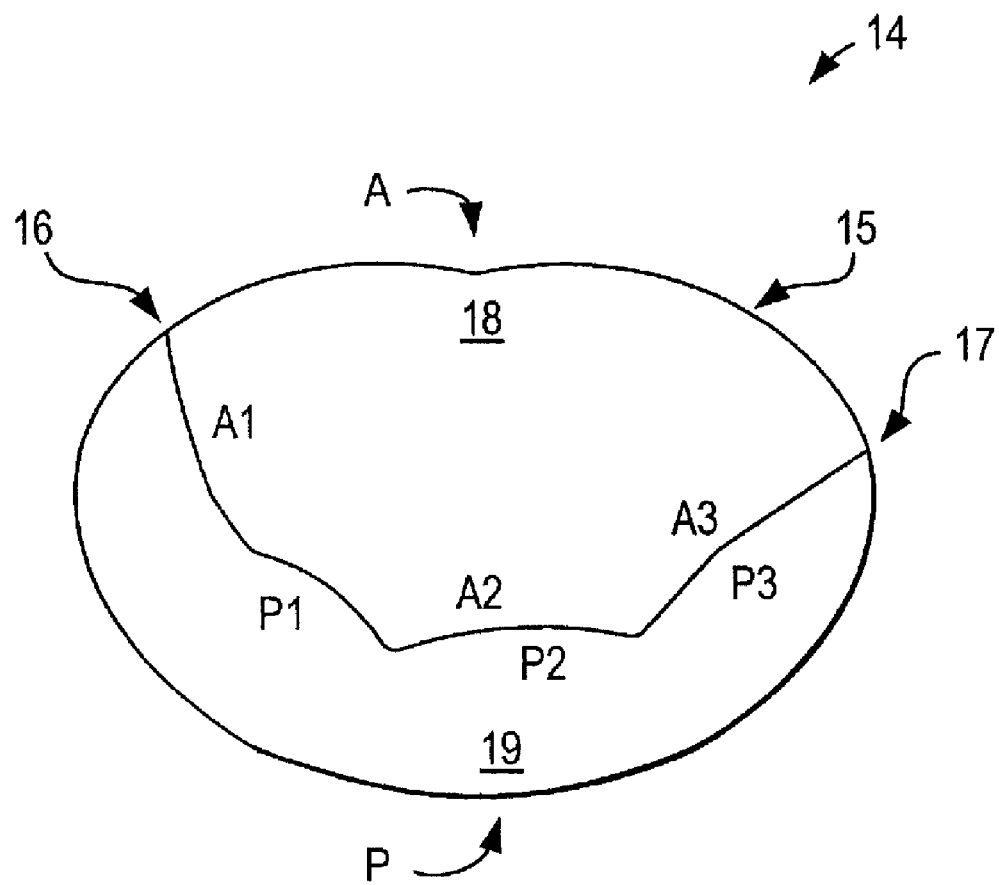
FIG. 1 is a simplified or schematic view of a normal mitral heart valve as viewed from the left atrium during surgery.
Figure 3:
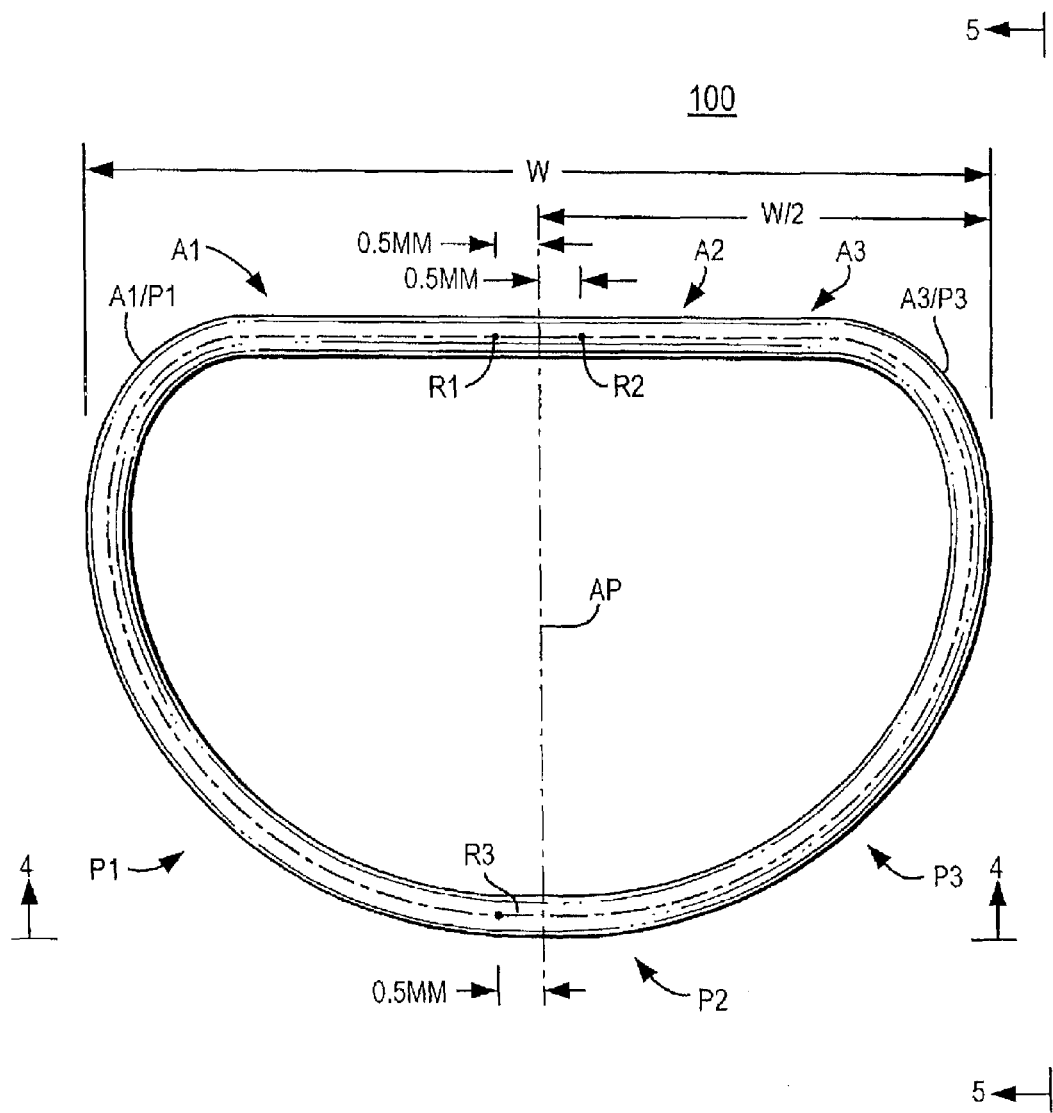
FIG. 3 is a simplified "plan" view of an illustrative embodiment of a mitral valve annuloplasty ring in accordance with the invention.
Figure 4:
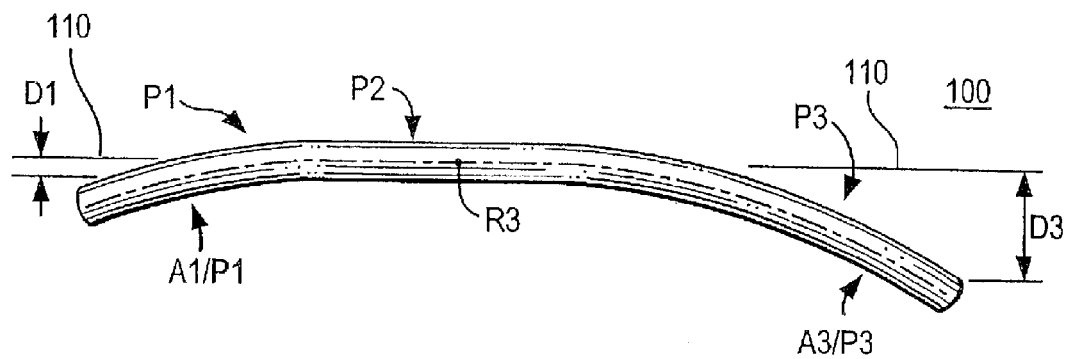
FIG. 4 is a simplified elevational view taken along the line 4-4 in FIG. 3.
Figure 5:
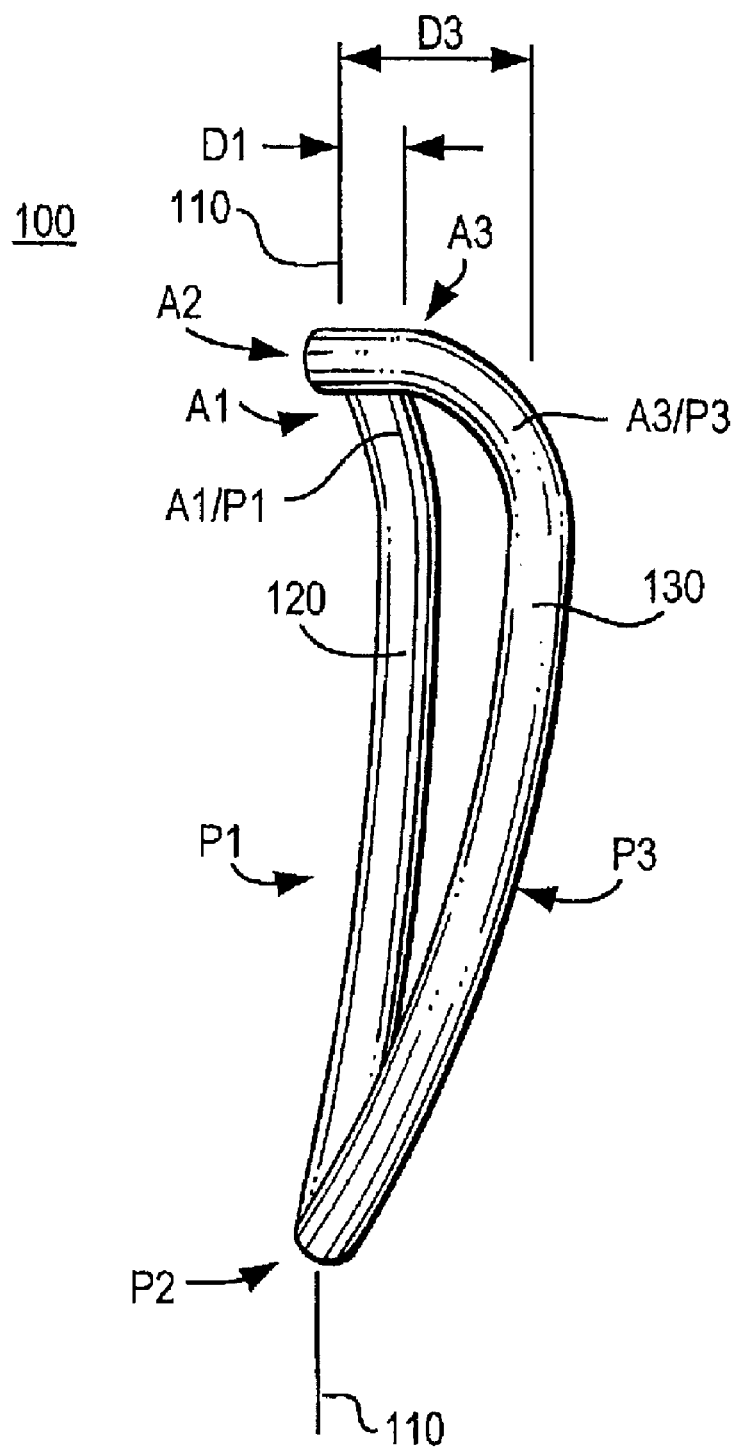
FIG. 5 is a simplified elevational view taken along the line 5-5 in FIG. 3. The scale of FIG. 5 is larger than the scale of FIG. 3.

An illustrative embodiment of a mitral valve annuloplasty ring 100, in accordance with the invention, that is better suited to treating patient conditions like those described in the background section of this specification is shown in FIGS. 3-5. FIG. 3 shows ring 100 in the same orientation as FIG. 1 shows a mitral valve to which ring 100 may be applied. FIG. 3 shows that ring 100 has a generally D shape. The relatively straight side of the D (toward the top in FIG. 3) is the anterior side of the ring in use. The curved side of the D (toward the bottom in FIG. 3) is the posterior side of the ring in use.

As shown in FIG. 3, ring 100 includes anterior segments A1, A2, and A3, and posterior segments P1, P2, and P3. Each of these segments is radially adjacent but beyond or outside the corresponding portion of the mitral valve leaflets when the ring is in use (i.e., implanted in a patient adjacent the annulus of the patient's mitral valve). Thus, for example, anterior ring segment A1 will be adjacent the base of the A1 segment of anterior leaflet 18 when ring 100 is in use. Similarly, posterior ring segment P1 will be adjacent the base of the P1 segment of posterior leaflet 19 when ring 100 is in use. The same correspondence between ring segments and leaflet segments applies to all ring segments all the way around ring 100. Thus it will be seen that ring 100 includes a closed loop series of segments A1, A2, A3, P3, P2, and P1, in that order.

In addition to defining ring segments as above, it is convenient to refer to several reference points on ring 100. Each of these reference points (A3/P3, A1/P1, R1, R2, and R3) is located on an axis that runs annularly around the ring and that passes coaxially through the center of the core material of the ring. The point A3/P3 is the point at which ring segments A3 and P3 join or meet one another. This point is adjacent the posterior commissure 17 (FIG. 1) of the mitral valve when ring 100 is in use. (The exact location of point A3/P3 along the ring is not critical. FIG. 3 thus tends to show the approximate locations of the various ring segments and points like A3/P3 and A1/P1. The locations of these features are, of course, generally as shown in FIG. 3.)

Another significant point on ring 100 is point A1/P1. This is the point at which segments A1 and P1 join or meet one another. When ring 100 is in use, point A1/P1 is adjacent the anterior commissure 16 (FIG. 1) of the mitral valve.

Other points on ring 100 are reference points R1, R2, and R3. These reference points are located as will now be described. Ring 100 has a so-called anterior-posterior ("AP") axis, which extends across the ring from its anterior side to its posterior side. The AP axis is located so that it is perpendicular to and bisects a line between reference points R1 and R2. Reference points R1 and R2 are located along the anterior side of the ring so that the AP axis bisects a greatest width dimension W of the ring, which greatest width dimension is measured perpendicular to the AP axis. Anterior-side reference point R1 is spaced to one side of the AP axis by 0.5 mm. Anterior-side reference point R2 is spaced to the other side of the AP axis by 0.5 mm. Reference point R3 is on the posterior side of the ring and is spaced to one side (e.g., the R1 side) of the AP axis by 0.5 mm. Reference points R1-R3 lie in and thereby define the location of a so-called reference plane.

(It should be noted that the "greatest width dimension" W is the perpendicular distance between two tangents to the ring that are both parallel to the AP axis and that are as far apart as possible on opposite sides of the ring. It is possible that there may be some distance across the ring, measured in some other way, that is greater than W, but that is irrelevant to the present invention and not what is meant by the "greatest width dimension" as used herein.)

FIG. 4 shows that ring 100 is not planar. In the particular embodiment shown in FIGS. 3-5, each of anterior ring segments A1, A2, and A3 is substantially out of sight behind the corresponding posterior ring segment P1, P2, and P3 in FIG. 4. This is not necessarily exactly the case in all embodiments, but it simplifies FIG. 4 and facilitates the present discussion. The reference plane referred to in the preceding paragraph is identified in FIG. 4 (and FIG. 5) by the reference number 110.

FIG. 4 shows ring segments A1 and P1 curving down and away from reference plane 110 as one proceeds to the left from a medial portion of what is visible in FIG. 4. FIG. 4 also shows ring segments A3 and P3 curving down and away from plane 110 as one proceeds to the right from the medial portion of FIG. 4.

Although points A1/P1 and A3/P3 are not per se visible in FIG. 4, their approximate left-right locations are indicated with arrows labeled A1/P1 and A3/P3, respectively. It will be apparent from this depiction that point A3/P3 is lower relative to plane 110 than point A1/P1. Thus dimension D3 (the distance of point A3/P3 below plane 110) is greater than dimension D1 (the distance of point A1/P1 below plane 110). Ring 100 is thus asymmetrical from left to right (as viewed in FIG. 4) in this respect.

FIG. 5 shows another view of ring 100 on an even larger scale than FIGS. 3 and 4 (see FIG. 3 for the orientation of FIG. 5 relative to FIGS. 3 and 4). FIG. 5 shows all the features of ring 100 that have been previously described. FIG. 5 again shows that the side of ring 100 that includes point A3/P3 is displaced farther from plane 110 than the side of the ring that includes point A1/P1. This is again shown in FIG. 5 by the fact that dimension D3 is greater than dimension D1.

Note in connection with FIG. 5, especially, that the displacement at point A1/P1 from reference plane 110 is not necessarily the greatest displacement of that side of the ring from that plane. Another point (like 120 in FIG. 5) along P1 may actually have greater displacement from plane 110 than point A1/P1. The same may be true on the other side of ring where point A3/P3 may not have that side's greatest displacement from plane 110. Another point 130 along P3 may have even greater displacement from plane 110. Nevertheless, it remains the case that point A3/P3 has greater displacement (D3) from plane 110 than point A1/P1 has. Local maximum displacement point 130 (if different from point A3/P3, as it is in ring 100) also has greater displacement from plane 110 than local maximum displacement point 120 (again assumed to be different than point A1/P1, as in ring 100). A possible embodiment is for point A3/P3 to have greater displacement from plane 110 than any point (even point 120) on the other side of the ring.

It will also be noted from what has been shown and described about ring 100 that, at a minimum, at least some portions of ring segments A3 and P3 curve, slope, or incline away from reference plane 110 (in the direction away from ring segments A2 and P2) in order for point A3/P3 to be displaced from that plane. Similarly, at least some portions of ring segments A1 and P1 curve, slope, or incline away from plane 110 (in the direction away from ring segments A2 and P2) in order for point A1/P1 to be displaced from that plane. Both the A1/P1 side of the ring and the A3/P3 side of the ring are displaced to the same side of plane 110. Ring 100 is thus saddle shaped. However, the displacement from plane 110 that is reached on the A3/P3 side of the ring is greater than the displacement that is reached on the A1/P1 side of the ring. The above-mentioned saddle shape is thus somewhat asymmetrical, with the A3/P3 side of the ring being more depressed than the A1/P1 side of the ring.

Figure 2:
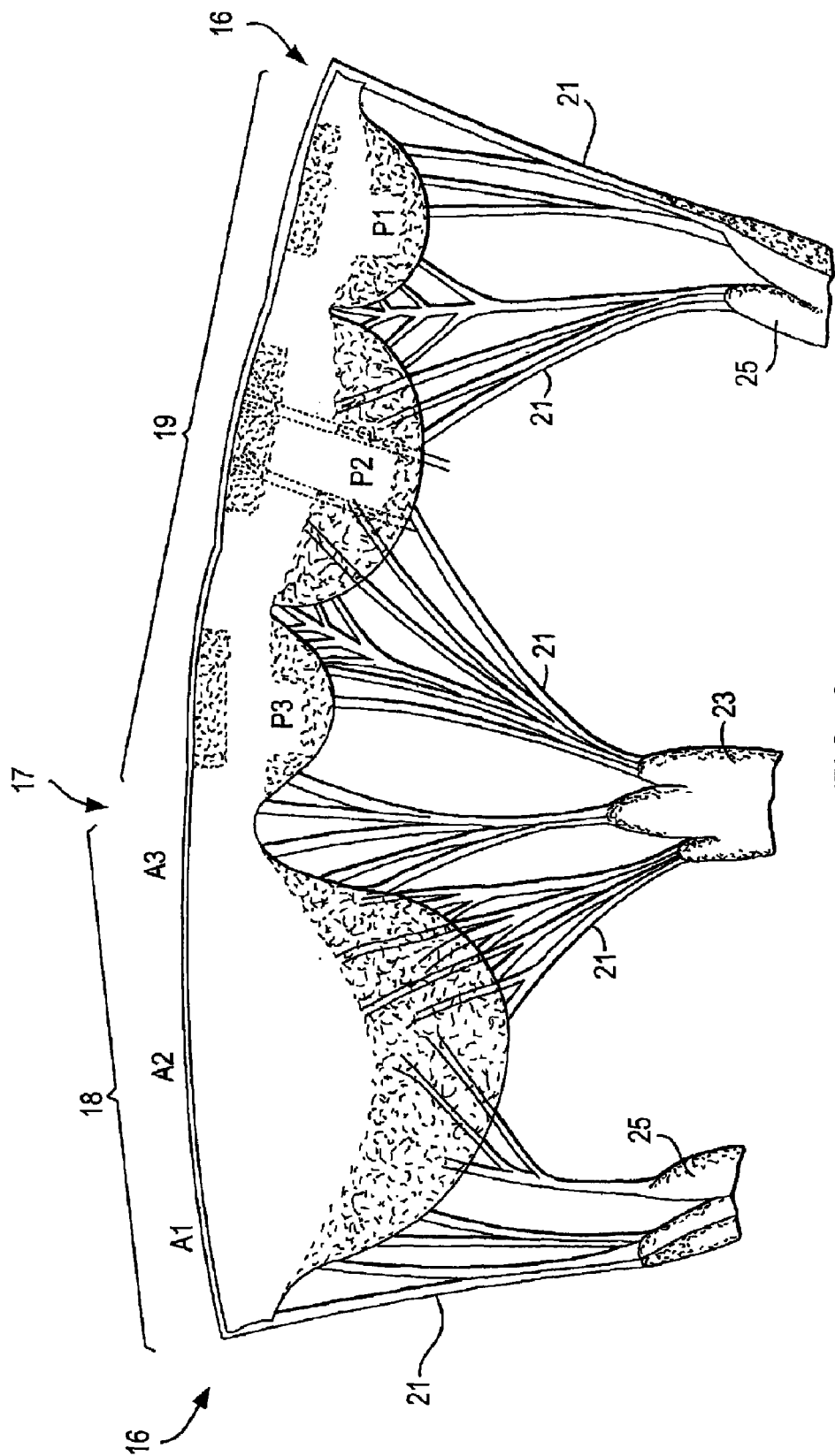
FIG. 2 is a simplified or schematic view of mitral heart valve structures that have been dissected vertically at the anterolateral commissure and splayed open.

The greater "downward" displacement of the side of ring 100 that includes point A3/P3 is of significant benefit in compensating for patient conditions like those described in the background section of this specification. Those conditions tend to downwardly displace tissue structures 23 (and their associated structures 21) more than tissue structures 25 (and their associated structures 21) (see again FIG. 2). Extra downward depression of the mitral valve annulus radially out from leaflet segments A3 and P3 (and including posterior commissure 17) may beneficially compensate for this problem. Such extra downward depression of this portion of the valve annulus is provided by ring 100, which has greater displacement from plane 110 on its side that includes segments A3 and P3 and point A3/P3 than on its other side (i.e., its side that includes segments A1 and P1 and point A1/P1).

Figure 6:
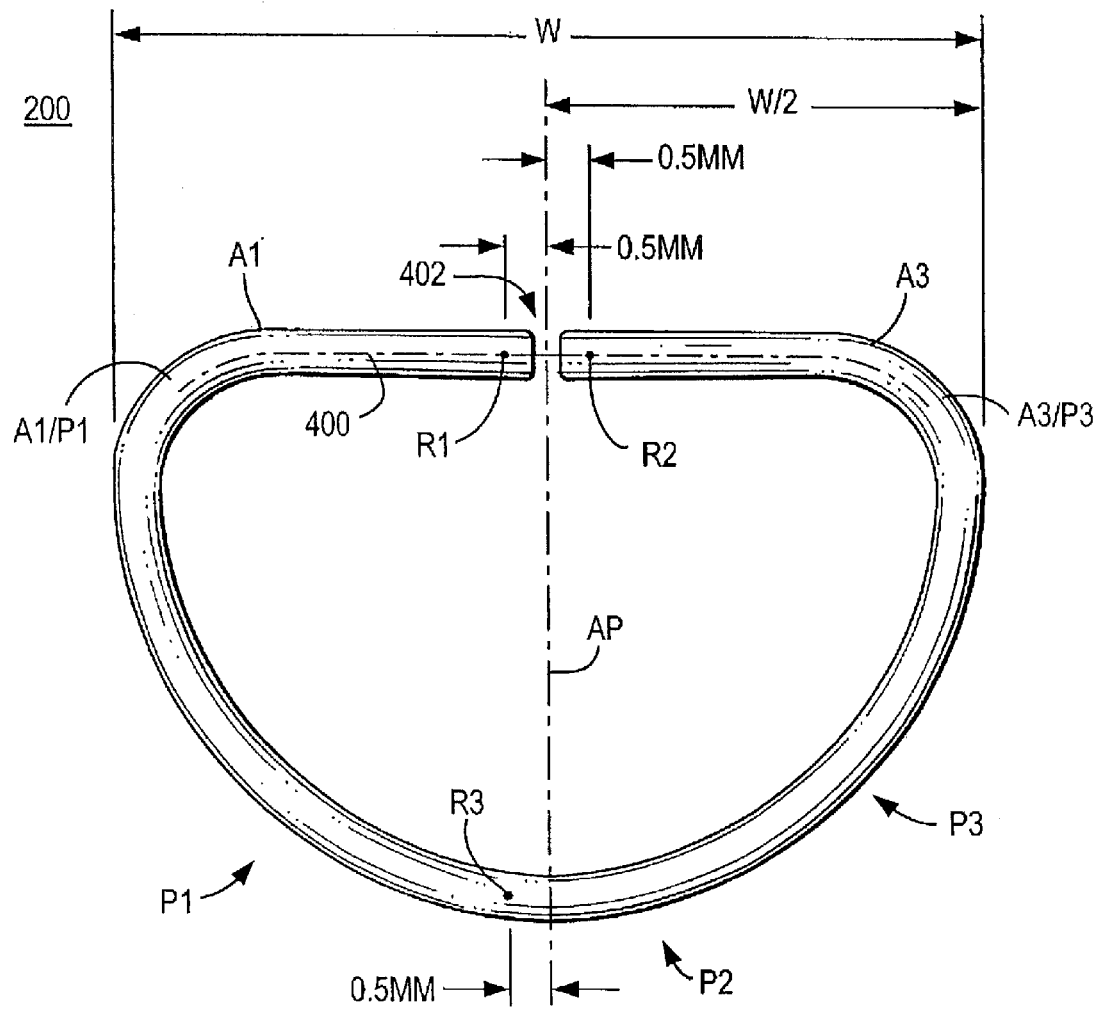
FIG. 6 is similar to FIG. 3, but shows an illustrative embodiment of a C-shaped mitral valve annuloplasty prosthesis in accordance with the invention.
Figure 7:
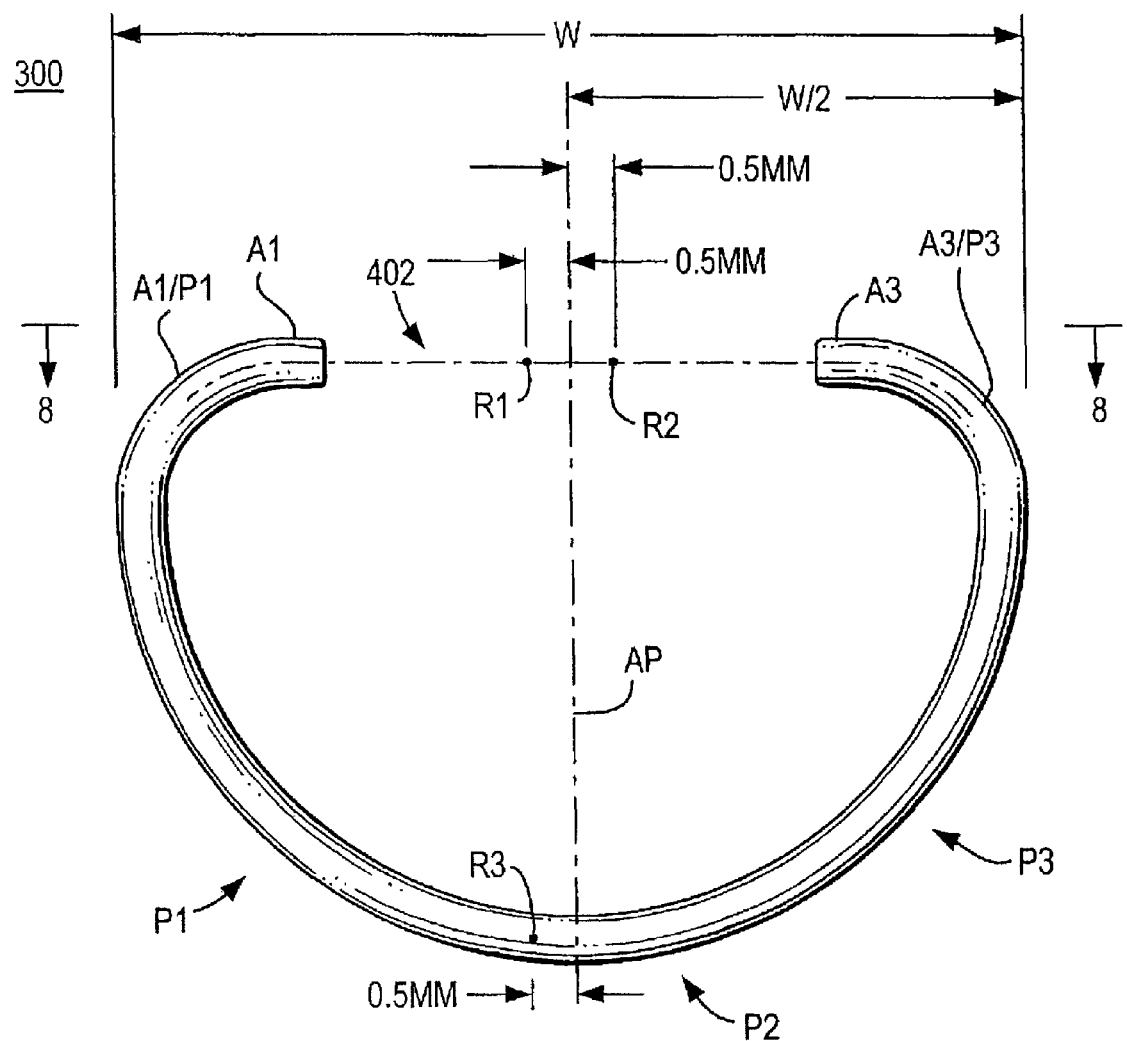
FIG. 7 is similar to FIG. 6, but shows another illustrative embodiment of a C-shaped mitral valve annuloplasty prosthesis in accordance with the invention.

It is known that mitral valve annuloplasty prostheses are not always complete rings like ring 100. For example, a portion of the anterior side of what would otherwise be a complete ring can be omitted to produce a C-shaped prosthesis. Examples of such Cs are shown in FIGS. 6 and 7. The C 200 in FIG. 6 has a relatively small gap 402 on the anterior side. The C 300 in FIG. 7 has a relatively large gap 402 on the anterior side. The anterior gap in FIG. 7 is approximately the maximum acceptable gap. Any amount of anterior-side gap (up to the approximate amount shown in FIG. 7) can be employed in C-shaped prostheses.

Figure 8:
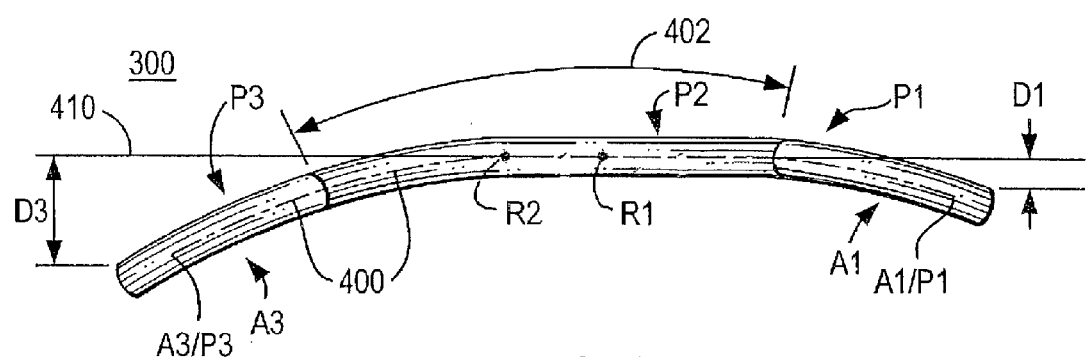
FIG. 8 is a view taken along the line 8-8 in FIG. 7.

The present invention can be applied to C-shaped prostheses like those exemplified by FIGS. 6 and 7. The portions of such a C-shaped prosthesis that are present in the C are shaped and disposed in three dimensions as though they were the corresponding portions of a complete ring in accordance with the invention (see also FIG. 8, which is another view of illustrative C shown in FIG. 7). In other words, a C-shaped prosthesis in accordance with the invention is shaped as though made from a complete ring in accordance with the invention, but with some of the anterior of the complete ring omitted to produce the C.

Although some portion of the anterior of a C in accordance with the invention has been omitted, it is possible to visualize a "trajectory" of the anterior side. Chain-dotted line 400 indicates such a trajectory in FIGS. 6-8. Note that trajectory 400 spans the entire anterior side of each C. Where the anterior side has structure or material (i.e., to the left and right of anterior gap 402), trajectory 400 passes coaxially and centrally along that structure. In gap 402 (where each C has no actual structure or material) trajectory 400 continues smoothly out of the material to one side of the gap, across the gap, and into the material on the other side of the gap. In other words, trajectory 402 follows the same path that the anterior side of the prosthesis 200 or 300 would have if it were a complete ring in accordance with the invention.

FIGS. 6 and 7 show that the same reference points R1 through R3 that are descried above in connection with ring 100 can be used again to define a reference plane 410 (see FIG. 8) that is useful in describing the shape of Cs in accordance with the invention. In the case of such Cs, however, it is appropriate to say that reference points R1 and R2 are on anterior trajectory 400. This is so because, depending on the size of gap 402, reference points R1 and R2 may be either in anterior material of the C (e.g., as in the case of FIG. 6) or in the anterior gap 402 (e.g., as in the case of FIG. 7). The anterior trajectory concept makes it possible to describe the locations of reference points R1 and R2 generically, regardless of the size of gap 402.

It is thus now possible to describe Cs in accordance with the invention (e.g., a C like 200 or 300) as including the following features: A1, P1, P2, P3, and A3 segments connected in series in that order; an anterior gap 402; an anterior trajectory 400 as described above; an anterior-to-posterior axis AP perpendicular to and bisecting a line between reference points R1 and R2, both of which are located along anterior trajectory 400; a greatest width dimension W measured perpendicular to the AP axis, reference points R1 and R2 and the AP axis being located so that the AP axis bisects the greatest width dimension; each of reference points R1 and R2 being spaced from the AP axis by 0.5 mm; reference point R3 on the posterior side of the C, spaced to one side of the AP axis by 0.5 mm, and defining with reference points R1 and R2 a reference plane 410; both of points A1/P1 (where the A1 and P1 segments meet) and A3/P3 (where the A3 and P3 segments meet) being spaced from reference plane 410 to the same side of that plane; and the spacing of point A3/P3 from reference plane 410 being greater than the spacing of point A1/P1 from that plane. Other features that are described above for complete rings in accordance with the invention are again applicable to Cs in accordance with the invention because the only significant difference between Cs and rings in accordance with the invention is the omission of a portion of the anterior side of a ring to produce a C. The therapeutic effects of Cs in accordance with the invention are similar to the therapeutic effects described above for rings in accordance with the invention.

A wide range of materials are well known for making annuloplasty prostheses, and any of the known materials that are suitable for making prostheses in accordance with this invention can be used. Examples of suitable materials include titanium, a titanium alloy, Elgiloy (a cobalt-nickel alloy), Nitinol (a nickel-titanium alloy), stainless steel, a cobalt-chromium alloy, a ceramic, and a polymer (e.g., ultra-high-molecular weight polyethylene, polyurethane, or the like). The prostheses of this invention (like ring 100 or Cs 200 or 300) can have any desired degree of rigidity, consistent with the objective of this invention for the prosthesis to apply significant forces in particular ways to various parts of the mitral valve annulus. For example, the prostheses of this invention can be rigid or substantially rigid. Alternatively, the prostheses of this invention may be capable of some plastic deformation if the surgeon wants to modify the prosthesis shape somewhat for a particular patient's anatomy. The prosthesis should not be plastically deformable by the patient's anatomy alone, but the prosthesis may be capable of some elastic deformation in response to the patient's anatomy, including changes in anatomical shapes as a result of body functions such as heartbeats. Nevertheless, a prosthesis that is capable of such flexibility should always be resiliently trying to return to an unloaded shape like that shown in the FIGS. herein. In that way, even a prosthesis that is capable of some flexibility is always applying the kind of therapeutic force to the mitral valve annulus that is desired in accordance with the invention.

Just as any of several materials are suitable for use as the basic material of the prostheses of this invention, the prostheses of this invention may also include other known annuloplasty prosthesis features. For example, the prostheses of this invention may be wrapped in or otherwise associated with fabric or other materials through which sutures can be passed as part of the process of implanting the prosthesis in a patient.

It will be understood that the foregoing is only illustrative of the principles of the invention, and that various modifications can be made by those skilled in the art. For example, certain aspects of the prosthesis shapes shown herein can be modified. As just one specific illustration of this, the ratio of greatest width to greatest height of the prosthesis (e.g., the horizontal and vertical dimensions, respectively, in FIG. 3) can be larger or smaller than what has been specifically shown.

The invention claimed is:

1. A method of treating a patient's mitral valve comprising: applying an annuloplasty prosthesis to the mitral valve adjacent the annulus of the mitral valve, the mitral valve including anterior and posterior valve commissures at which a first native valve leaflet and a second native valve leaflet are attached, the annuloplasty prosthesis dipping down adjacent the anterior and posterior valve commissures relative to at least some other portions of the annulus between the commissures, the annuloplasty prosthesis pushing down the portion of the annulus that is adjacent to the posterior commissure farther than the prosthesis dips down adjacent the anterior commissure such that the effect of the prosthesis along the first native valve leaflet and the second native valve leaflet is asymmetrical.

2. The method defined in claim 1 wherein the prosthesis comprises a complete ring.

3. The method defined in claim 2, wherein the mitral valve includes an anterior portion including A1, A2, and A3 segments along an edge of the first native valve leaflet adjacent the annulus between the anterior and posterior valve commissures and wherein the mitral valve includes a posterior portion including P1, P2, and P3 segments along an edge of the second native valve leaflet adjacent the annulus between the anterior and posterior valve commissures, the segments being connected in the order A1, A2, A3, P3, P2, and P1, such that the A1 and P1 segments meet and the A3 and P3 segments meet, and the method further comprising applying the ring such that the ring dips down adjacent at least a portion of each of the A1, A3, P1, and P3 segments of the valve leaflets relative to said portion of the annulus that is adjacent the A2 segment and said portion of the annulus that is adjacent the P2 segment.

4. The method defined in claim 1 wherein the mitral valve includes an anterior portion including A1, A2, and A3 segments along an edge of the first native valve leaflet adjacent the annulus between the anterior and posterior valve commissures and wherein the mitral valve includes a posterior portion including P1, P2, and P3 segments along an edge of the second native valve leaflet adjacent the annulus between the anterior and posterior valve commissures, the segments being connected in the order A1, A2, A3, P3, P2, and P1, such that the A1 and P1 segments meet and the A3 and P3 segments meet, the annuloplasty prosthesis having corresponding A1, A2, A3, P3, P2, and P1 segments being adapted for attachment to the annulus of a patient's mitral valve adjacent respective A1, A2, A3, P3, P2, and P1 leaflet portions of the mitral valve, such that the A1 and P1 segments of the annuloplasty prosthesis meet directly adjacent to the anterior commissure of the mitral valve and the A3 and P3 segments meet directly adjacent to the posterior commissure of the mitral valve when the annuloplasty prosthesis is attached to the annulus of the patient's mitral valve.

5. The method defined in claim 1, the mitral valve includes an anterior portion comprising A1, A2, and A3 segments along an edge of the first native valve leaflet adjacent the annulus between the anterior and posterior valve commissures and wherein the mitral valve includes a posterior portion including P1, P2, and P3 segments along an edge of the second native valve leaflet adjacent the annulus between the anterior and posterior valve commissures, the segments being connected in the order A1, A2, A3, P3, P2, and P1, such that the A1 and P1 segments meet and the A3 and P3 segments meet, and wherein the prosthesis is a C-shaped prosthesis having a gap adjacent at least a portion of the A2 segment.

* * * * *